United States Patent [19]

Schwartz et al.

[11] Patent Number: 5,092,844
[45] Date of Patent: Mar. 3, 1992

[54] INTRACATHETER PERFUSION PUMP APPARATUS AND METHOD

[75] Inventors: Robert S. Schwartz; Joseph G. Murphy, both of Rochester, Minn.

[73] Assignee: Mayo Foundation for Medical Education and Research, Rochester, Minn.

[21] Appl. No.: 507,155

[22] Filed: Apr. 10, 1990

[51] Int. Cl.$^5$ .............................................. A61M 1/00
[52] U.S. Cl. ...................................... 604/151; 600/16
[58] Field of Search .................... 604/151, 135, 152; 623/3; 600/16; 417/417

[56] References Cited

U.S. PATENT DOCUMENTS

| | | |
|---|---|---|
| 3,592,184 | 7/1971 | Watkins et al. . |
| 3,889,686 | 6/1975 | Duturbure . |
| 3,923,065 | 12/1975 | Nozick et al. . |
| 4,213,461 | 7/1980 | Pevsner . |
| 4,407,271 | 10/1983 | Schiff . |
| 4,445,892 | 5/1984 | Husselm et al. . |
| 4,471,779 | 9/1984 | Antoshkiw et al. . |
| 4,581,017 | 4/1986 | Sobota . |
| 4,610,662 | 9/1986 | Weikl et al. . |
| 4,625,712 | 12/1986 | Wampler ................................. 623/3 |
| 4,646,742 | 3/1987 | Packard et al. . |
| 4,657,536 | 4/1987 | Dorman . |
| 4,666,426 | 5/1987 | Aigner . |
| 4,753,221 | 6/1988 | Kensey et al. ....................... 604/151 |
| 4,753,640 | 6/1988 | Nichols et al. . |
| 4,817,586 | 4/1989 | Wampler ............................. 604/151 |
| 4,857,054 | 8/1989 | Helfer . |
| 4,919,647 | 4/1990 | Nash .................................... 604/151 |
| 4,944,722 | 7/1990 | Carriker et al. ....................... 600/16 |
| 4,957,504 | 9/1990 | Chardack ............................. 600/16 |
| 4,964,864 | 10/1990 | Summers et al. ..................... 600/16 |
| 4,969,865 | 11/1990 | Hwang et al. ....................... 604/151 |

FOREIGN PATENT DOCUMENTS 0192575 2/1986 France .

Primary Examiner—Paul J. Hirsch
Attorney, Agent, or Firm—Merchant, Gould, Smith, Edell, Welter & Schmidt

[57] ABSTRACT

An intracatheter pump apparatus and method is described for infusing fluids through a lumen of a catheter. The intracatheter pump includes a motor or power source on the outside of the catheter which causes movement of a fluid moving mechanism positioned in the lumen of the catheter, the fluid moving mechanism being attached to the distal end of an elongated member which in turn is attached to the motor.

15 Claims, 2 Drawing Sheets

INTRACATHETER PERFUSION PUMP APPARATUS AND METHOD

FIELD OF THE INVENTION

The present invention relates to an intracatheter pump apparatus and method for perfusing fluids such as blood through a lumen of a catheter or the like.

BACKGROUND OF INVENTION

Catheters are commonly used invasively to treat diseased vessels in animal and human bodies. Cardiovascular diseases are one of the most common diseases treated by the use of catheters. Catheters are used to counter atherosclerosis, one of the effects of cardiovascular disease, through a procedure known as balloon angioplasty wherein a balloon is inflated in the diseased vessel at a location where a narrowing of the vessel has occurred.

It will be appreciated, that in addition to angioplasty, there are numerous other uses of catheters in a living being such as treatment of the urinary tract, brain, lungs, kidneys, liver, etc.

In some of these treatments, it is often necessary to have a relatively long term occlusion due to angioplasty balloon inflation within a body vessel, which prevents fluid flow through the vessel externally of the catheter. For example, it is not uncommon to have a blockage, due to inflation of the catheter balloon, occurring for more than ten seconds. In certain situations, such as severe coronary artery disease, no interruption of blood flow can be safely tolerated.

For this reason, perfusion catheters have been constructed which are adapted to pass blood through the catheter even though the catheter is acting to block flow externally to the catheter in the area of the vessel which is being treated, multiple areas of the vessel being treated in some situations. Perfusion catheters are of two general types. Perfusion balloon catheters have an inflatable angioplasty balloon attached and are typically used to enable perfusion of blood through the catheter when the angioplasty balloon is inflated during vessel dilation. Perfusion "bailout" catheters do not have a balloon attached and are typically used in emergency situations when there is a vessel dissection or tear post angioplasty. Perfusion "bailout" catheters have proximal and distal side-holes and function as a temporary stenting device to hold the vessel open until the patient is otherwise treated, such as by emergency bypass surgery.

Typical perfusion catheters have one or more simple apertures upstream of the treatment or blockage site, and one or more apertures downstream. See for example, U.S. Pat. No. 4,581,017, FIG. 2. Such catheters have a rate of flow though that is primarily controlled by the diameter of the flow lumens within the catheter, the pressure difference across the lumens, viscosity of the fluid used, the length of the catheter tube, etc. These perfusion catheters often do not provide the high fluid flow rate required through the vessel during the blockage by the catheter balloon. As a result, treatments requiring a more extended blockage of the vessel are risky, since even with the perfusion provided, the flow downstream of the catheter is less than the needed flow. The blood pressure may also be too low to support good flow.

U.S. Pat. No. 4,857,054 discloses an attempt to overcome this problem. This patent discloses a perfusion angioplasty catheter with pump assist. The catheter includes a tube having a distal end including means for effecting angioplasty treatment of a body vessel, and a proximal end containing control means. The tube of the catheter further includes a perfusion lumen extending most of the length of the tube and means in the tube adjacent the distal end defining a plurality of apertures, on both sides of the catheter balloon, providing for fluid movement from or to the lumen past the balloon. The catheter includes a plurality of one way valves each disposed proximate one of the apertures. At least one of the valves is constructed to admit fluids only into the lumen from the body vessel and at least one of the other valves being constructed to permit fluid only to the body vessel from the lumen. The control means is located external of the body and controls a pump which is also external of the body for pumping a fluid such as a saline solution or a blood substitute into the perfusion lumen. As the pump pumps fluid into the perfusion lumen, blood is forced out of the perfusion lumen and into the body vessel. As the pump withdraws the fluid, blood is caused to flow into the perfusion lumen. In this fashion, the pump assists blood flow through the catheter around the obstructed site in the body vessel. Some disadvantages associated with this design is that fluid flow can only occur in one direction. Moreover, the pump is on the outside of the body. Also, the relatively long fluid flow path and the fluid viscosity, would seem to make it difficult to ensure adequate fluid flow.

The present invention solves many of the problems associated with current perfusion catheter systems.

SUMMARY OF THE INVENTION

The present invention relates to an intracatheter perfusion pump.

One embodiment of the present invention includes a pump apparatus for pumping fluids into and out of a lumen of a catheter. The pump apparatus includes an elongated member having a proximal end and a distal end. The elongated member is positionable in the lumen of the catheter. A motor is connected to the proximal end of the elongated member for moving the elongated member. A fluid moving mechanism is attached to the elongated member proximate the distal end such that when the fluid moving mechanism is moved by the elongated member, the fluid moving mechanism causes longitudinal movement of fluids through the lumen.

In one embodiment of the present invention the fluid moving mechanism has a helical configuration.

In yet another embodiment of the present invention the fluid moving mechanism includes an elongated cylindrical member having a ridge encircling about the circumference thereof in a longitudinal helix arrangement whereby as the elongated member is rotated by the motor, the pump apparatus will pump fluids.

In still another embodiment of the present invention, the fluid moving mechanism includes a substantially flat ribbon member twisted in a longitudinal helical pattern.

In one embodiment of the present invention the elongated member is rotatable at different rates by the source of power so as to cause movement of the fluid at different rates.

In one embodiment of the present invention the fluid moving mechanism includes a rotor attached to the elongated member proximate the distal end.

In yet in another embodiment of the present invention, the fluid moving mechanism includes an impeller which pulls fluid in the direction of desired fluid flow as the elongated member is rotated.

Yet another embodiment of the present invention includes a propeller which pushes fluid in the direction of desired fluid flow as the elongated member is rotated.

Still another embodiment of the present invention includes a pump apparatus for pumping the fluids into and out of a lumen of a catheter wherein the motor is mechanically connected to the proximal end of the elongated member for causing longitudinal reciprocating motion of the elongated member.

In one embodiment of the present invention the fluid moving mechanism comprises a piston.

In yet another embodiment of the present invention the fluid moving mechanism comprises a diaphragm.

An advantage of one embodiment of the present invention is that is it is bidirectional or capable of moving fluid in either direction within the lumen of the catheter.

The present invention also relates to a method of pumping fluids through a section of a catheter lumen, the lumen having at least two longitudinally spaced apart fluid communication ports, the method comprising the steps of inserting an elongated wire having a fluid moving mechanism attached to a distal end thereof, into the lumen of the catheter and moving the elongated wire such that the fluid moving mechanism moves fluid longitudinally of the lumen between the two longitudinally spaced apart ports.

One embodiment is particularly advantageous in that the distal end of the perfusion lumen is open such that the present invention can be threaded over a conventional guide wire in emergencies where a guide wire is already in place. A guide wire is typically 0.010 to 0.018 inches in diameter and typically constructed with a soft-tip platinum wire tip in a spring configuration. The guide wire is inserted into the vessel and positioned proximate the site in the vessel to be treated. All other devices, such as catheters, must "railroad" along the guide wire to the treatment site. Once, the perfusion catheter has been fed along the guide wire and is properly positioned within the vessel, the guide wire is withdrawn since typically the guide wire lumen of the catheter and the perfusion lumen of the catheter are one and the same. In one embodiment of the present invention, the perfusion lumen of the catheter can function as a guide wire lumen for insertion of a conventional guide wire.

Still another advantage of one embodiment of the present invention is that the elongated member and the fluid moving mechanism can be designed to also function as a conventional guide wire for positioning in the body vessel thereby providing two distinct functions, an intracatheter pump apparatus and a guide wire. This is particularly advantageous in that it does away with the need for a separate guide wire.

A particular advantage of the present invention is that the fluid moving mechanism or active pumping element of the pump is located in the lumen of the catheter and not external to the catheter.

Still another advantage of one embodiment of the present invention is that it allows for bidirectional fluid flow which is advantageous in several situations.

Another advantage of one embodiment of the present invention is that it routinely operates at low pressures below thirty (30) mm of Hg and even in cases where there is substantially no pressure, so as to provide a needed fluid flow rate. Preferred embodiments of the present invention provide a fluid flow rate of five to sixteen cubic centimeters per minute (5-16 cc/min).

Additionally, the present invention is readily adaptable for use with small, flexible and removable catheters and does not require large, bulky catheters for insertion of the pump apparatus.

Still another advantage of the present invention is that it provides adjustable, high flows of fluid regardless of the pressure in the vessel.

Yet another advantage of one embodiment of the present invention is that it does not require blood drawn from a remote site.

A preferred embodiment of the present invention allows the insertion of the elongated member and its fluid moving mechanism into and through a lumen of a catheter already in place in a vessel.

Still another advantage of the present invention is that it can be readily battery operated to facilitate portability and because of its simplicity will be inexpensive to produce.

Another advantage of the present invention is that simple modification of standard balloon catheters; i.e., adding apertures/ports on the proximal and distal sides of the balloon, will allow them to be used with the intracatheter perfusion pump of the present invention.

For a better understanding of the invention, its advantages, and the objects obtained by its use, reference should be made to the accompanying drawings and descriptive matter which form a further part hereof, and which there is illustrated and described a preferred embodiment(s) of the invention.

BRIEF DESCRIPTION OF THE DRAWINGS

Referring now to the drawings wherein corresponding reference numerals generally indicate corresponding elements throughout the several views.

DETAILED DESCRIPTION OF THE PREFERRED EMBODIMENT

Figure 1:
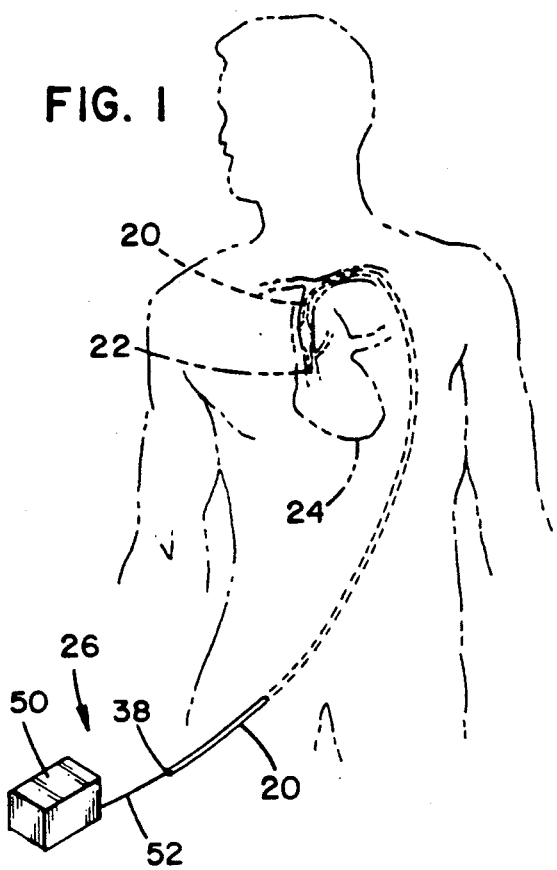
FIG. 1 is a schematic illustration of a use of an intracatheter perfusion pump in accordance with the principals of the invention to treat conditions at locations remote from the incision used to insert the catheter, by way of example a vessel of the heart is illustrated as being treated in this figure.

As generally illustrated in FIG. 1, the invention is described herein with respect to angioplasty treatment in an artery, wherein blood is the perfused body fluid.

In FIG. 1, the present invention is shown used with a balloon catheter 20 being used to treat a vessel 22 of a heart 24. However, it will be appreciated that the present invention is applicable to numerous types of treatments in various body vessels in which fluid needs to be perfused; e.g., vessels of the urinary tract, lungs, brain, kidneys, liver, etc.

As used herein, "angioplasty treatment" refers to any technique for increasing the cross sectional area of a body vessel. However, the present invention has application with various types of catheters and is not limited solely to angioplasty treatment. For example, the present invention might be used with "bailout" catheters. "Bailout" catheters do not have a balloon attached and are used in emergency situations when there is a vessel dissection or tear post angioplasty. The "bailout" catheter acts as a temporary stenting device to hold the vessel open until the patient is otherwise treated, usually by emergency bypass surgery.

The embodiments of the intracatheter perfusion pump 26 shown are illustrated as being positioned in the angioplasty catheter 20, also referred to as a balloon catheter. The catheter 20 has longitudinally spaced apart distal ports 30 and proximal ports 32 on distal and proximal sides of a balloon 34 of the catheter. The catheter shown is opened at a distal end 36 so as to be readily inserted over existing guide wires. The distal end 36 of the catheter shown, is constructed to travel within a body vessel and includes a proximal end 38 which typically remains out side the body.

The distal and proximal ends 36,38 of the catheter 20 are connected by a flexible tube 40 defining the body portion of the catheter 20. The tube 40 is highly flexible and encloses at least a perfusion lumen 42 that extends from the proximal end 38 to the distal end 36 inside the tube 40. Preferably, the tube 40 also encloses at least one, and most preferably, two additional lumens (not shown). The additional lumens are used to inflate and deflate the catheter balloon 34 via apertures, as is conventional, located adjacent the balloon 34. Additional lumens might be present for delivering medicant to the body vessel 22.

Figure 6:
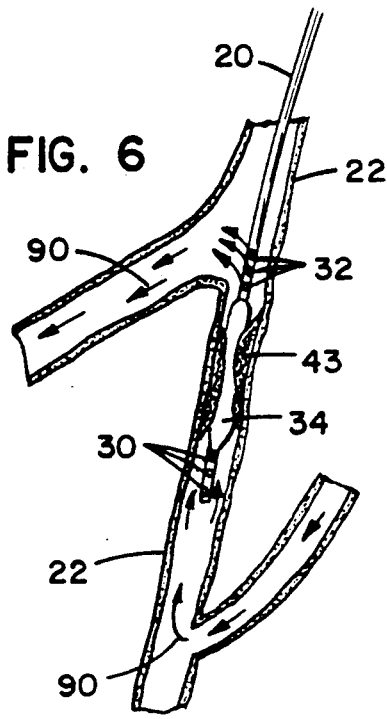
FIG. 6 is a schematic view illustrating the pumping of blood in an opposite direction from that shown in FIGS. 2 thru 5B.

While only a single balloon is shown, there may be more than one balloon. The balloon 34 treats the body vessel 22, by fracturing plaque buildup 43 in the vessel 22. This is probably best illustrated in FIG. 6. The balloon 34 is typically only partially inflated. Alternatively, one or both of the other lumens is used to effect other conventional treatments at the distal end (not shown), for example, to deliver laser light to illuminate a surface, to deliver a control wire for bending the distal end to make course corrections, for delivering medicant, and like.

At the proximal end 38 of the catheter, a motor 50 is provided for causing movement of a flexible elongated member 52 which is inserted into the catheter 20. The motor 50 might be powered in any number of ways such as by batteries, conventional alternating current (AC), air turbine, etc. and might cause a plurality of different movements and further might operate a different speeds selectable by the operator. Attached to the distal end of the elongated member 52 is a fluid moving mechanism 54, also referred to as the active pumping element, for pumping fluid such as blood through the lumen 42 between the distal and proximal ports 30,32 on opposite sides of the balloon 34. The elongated member 52 functions as an, extended flexible drive shaft interconnecting a drive shaft of the motor 50 to the fluid moving mechanism 54. The elongated member 52 might be constructed in any number of ways; e.g., as a wire, a cable, etc. The elongated member 52 and the fluid moving mechanism are made of suitable materials compatible with body fluids.

It will be appreciated that the intracatheter pump apparatus 26 of the present invention might take on several different forms. For example, the pumping element 52 might include a reciprocating pump element, a rotary pump element, a diaphragm pump element, a peristaltic pump element, a centrifugal element pump element, etc.

It will be appreciated that conventional materials compatible with the body can be utilized for the catheter 20, the elongated member 52, and the fluid moving mechanism 54. A variety of sizes might be used, with one example of a catheter having a channel diameter of 0.020 inches with the elongated member 52 having a diameter of approximately 0.014 inches to 0.016 inches as required, or even larger.

Figure 2:
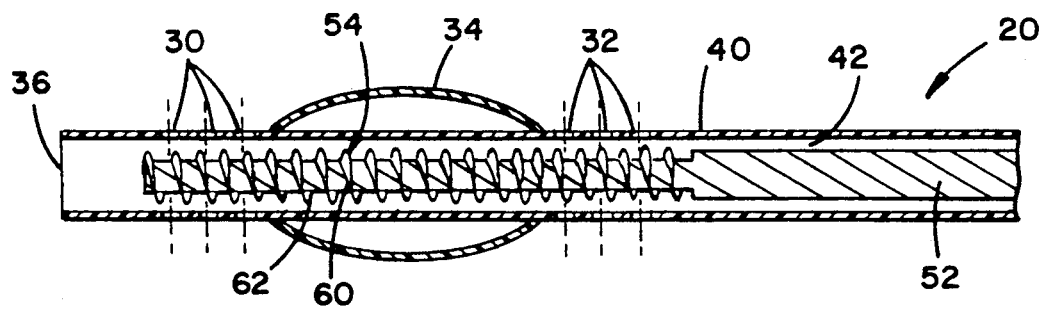
FIG. 2 is a partial longitudinal sectional view through a catheter constructed in accordance with the principles of the present invention and including an intracatheter perfusion pump in accordance with the principles of the present invention.

In the embodiment shown on FIG. 2, the fluid moving mechanism 54 or pumping element includes a cylindrical elongated member portion 60, of lesser diameter than the elongated member 52, with a ridge 62 on it in a longitudinal helix arrangement such that rotation of the elongated member 60 with the ridge causes movement of fluid such as blood in a desired direction which might be from right to left or left to right when looking at FIG. 2, depending on the direction of rotation of the elongated member 52. It will be appreciated, that the embodiment shown is bi-directional in that it can cause fluid movement in either longitudinal direction. The longitudinal helix might extend out beyond the end of the catheter 20 or it might be positioned entirely within the catheter 20. Very high rotational speeds can be achieved with the present invention; e.g., forty to fifty thousand revolutions per minute (rpm). Of course the specific configuration of the longitudinal helix such as the diameter of the ridges 62 and the elongated member portion 60, the height of the ridges 62, the pitch of the ridges 62, the distance between them, etc., the nature of the fluid being pumped, the amount of fluid flow desired, the pressure differential in the vessel between the distal and proximal ports 30,32, etc. will determine the desired rotational rate. In some situations a rotational rate of ten to twenty rpm might be sufficient. Moreover, the rate of fluid pumping can be varied as desired. Rotation of the longitudinal helix in a clockwise direction will cause fluid flow from right to left when looking at FIG. 2 while rotation in a counterclockwise direction will cause fluid flow from left to right. In the embodiment shown, the distal and proximal 30,32 ports are bidirectional so as to allow fluid flow either into or out of the lumen 42 of the catheter 20. Of course, the present invention will also work with one way ports.

Figure 3:
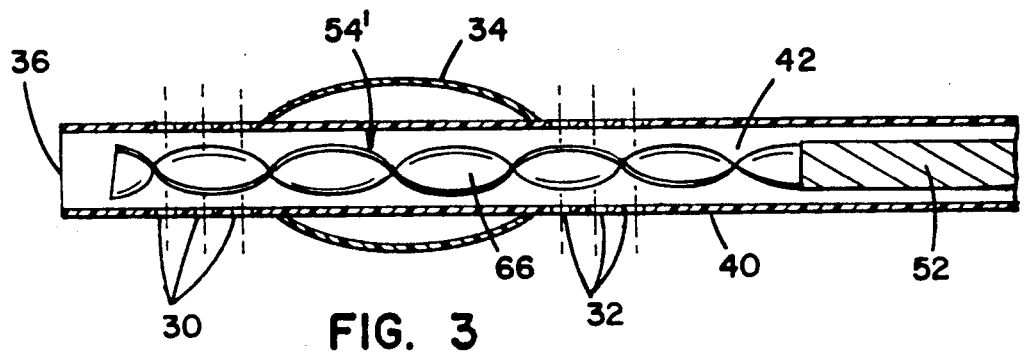
FIG. 3 is a view similar to FIG. 2 of an alternate embodiment of the intracatheter perfusion pump.

Illustrated in FIG. 3 is an alternative embodiment wherein the fluid moving mechanism, referred to by reference numeral 54', has a configuration similar to that of a twisted ribbon 66. Once again, depending on the specific configuration of the twisted ribbon 66, such as its pitch, etc. and the speed at which it is rotated will determine how much fluid is pumped through the lumen 42 within a given period of time. The fluid moving mechanism of this embodiment will typically occupy less volume of the catheter lumen 42 and thus allow more lumen for fluid flow. The twisted ribbon 66, as with the other parts of the invention, might be made of a material such as a metal which is compatible with body fluids.

Figure 4:
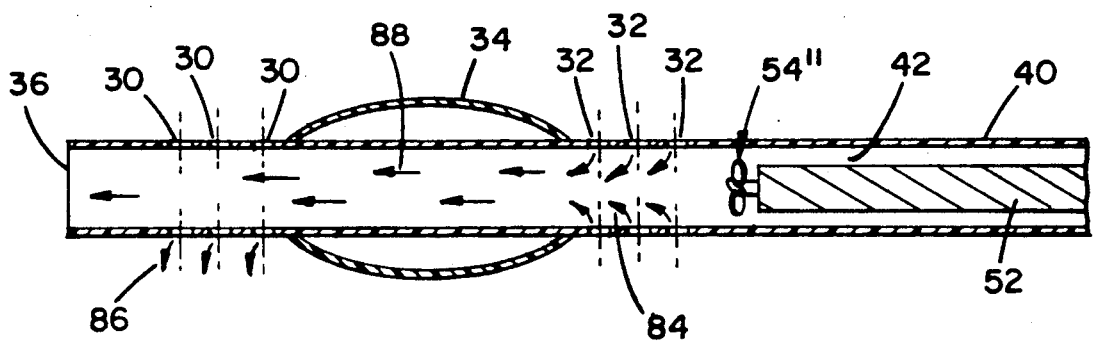
FIG. 4 is a view similar FIG. 2 of yet another alternate embodiment of an intracatheter perfusion pump in accordance with the principals of the present invention.

Illustrated in FIG. 4 is yet another embodiment of a fluid moving mechanism, referred to by reference numeral 54", in accordance with the principles of the present invention. In this configuration, the fluid moving mechanism 54" includes an impeller 70 attached to the end of the elongated member 52 proximate the proximal ports 32. When rotated, the impeller 70 creates a positive pressure which causes fluid flow through the lumen 42 between the ports 32,30, the flow of blood into and out of the lumen being indicated by arrows 72. In this embodiment, the lumen 42 between the ports 32,30 of the catheter 20 is completely unobstructed so as to allow more lumen area for the unobstructed flow of fluid such as blood therethrough. Once again, the rotational rate of the impeller 70 will depend on several factors as noted above in the discussions of the other embodiments. Rotation of twentyfive rpm might be sufficient in some situations. It will be appreciated that the exact positioning of the impeller 70 will also vary depending on the specific application. Negative pressure from the impeller will be used to prime the system.

Figure 5A:
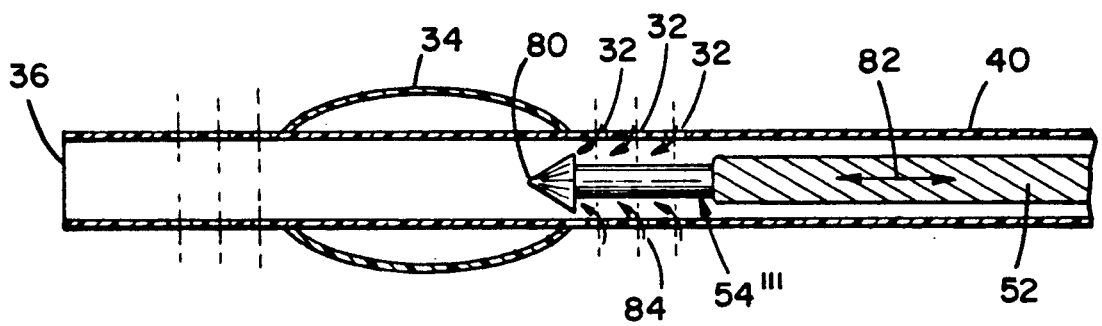
FIG. 5A is a view similar to FIG. 2 of still another alternate embodiment of an intracatheter perfusion pump in accordance with the present invention, the pump being shown in a retracted position.
Figure 5B:
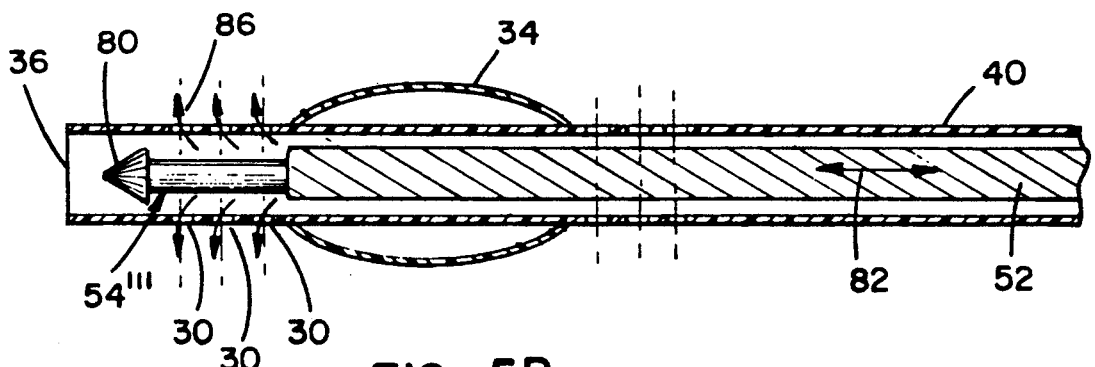
FIG. 5B is a view similar to FIG. 5A illustrating the pump in an extended position.

Illustrated in FIGS. 5A,B, is yet another embodiment of an intracatheter pump apparatus in accordance with the principles of the present invention. In this embodiment, the fluid moving mechanism, generally referred to by 54''', includes a piston 80 which is attached to the end of the elongated member 52. The motor 50 causes reciprocating longitudinal movement of the elongated member 52, as is illustrated by arrows 82, and thus the piston 80 in the catheter 20. The reciprocating motion of the elongated member 52 might be caused by any of a number of well known techniques for causing a reciprocating action, such as by use of a cam arrangement. The reciprocating movement or asymmetric travel of the piston 80 at the end of the elongated member 52 allows inflow of blood, as generally shown by arrows 84, into the lumen 42 upon retraction of the piston 80. The piston 80 is then rapidly pushed forward a predetermined distance to force the blood out of the distal ports 30, as generally illustrated by arrows 86, back into the body vessel. If the forward longitudinal movement of the piston 80 is preferably kept relatively short, compared with the piston's at rest position, then the flow of the blood as generally indicated by arrows 88, can be kept unidirectional. Once the elongated member 52 is past the proximal ports 30, blood will be caused to travel forward in the lumen 42. Upon return of the piston 80 to the at rest position, also referred to as the at rest position, a small vacuum will be created in the lumen 42 to help facilitate filling of the lumen 42 with blood. Use of an asymmetric cycle will assure that most blood will be propelled forward in the lumen. Once again, amount of flow will depend on the frequency of the reciprocating action, the length of the piston stroke, the configuration of the piston 80, etc. As with the other components, the piston 80 might be made out of any body fluid compatible material; e.g., teflon, polyurethane (PET), etc.

In FIGS. 2 thru 5B, the intracatheter pump 26 has been shown pumping fluid in a direction away from the elongated member 52 toward the distal end 36 of the catheter 20. However, a particular advantage of the present invention is that it can be used to pump fluid in the opposite direction. This is diagrammatically illustrated in FIG. 6, wherein blood is shown by arrows 90 as being pumped in a direction toward the proximal end 38 of the catheter 20. This change of direction in fluid flow is accomplished by changing the direction of rotation of the elongated member 52 for the embodiments shown in FIGS. 2 and 3.

Use of the present invention will now be discussed. As previously mentioned, the present invention is particularly advantageous in that it can be inserted into a balloon catheter 20 already in place. Moreover, the intracatheter pump apparatus 26 of the present invention most likely can be used with many existing perfusion balloon catheters which have proximal and distal ports 32,30 on opposite sides of the balloon 34. If the pump apparatus is used with a catheter already in place, it is simply inserted into the lumen 42 of the catheter 20 having the proximal and distal ports 32,30 and is then guided to the location where the balloon 34 is by any of several well known techniques. Once the fluid moving mechanism 54 of the pump apparatus 26 is properly positioned relative to the balloon 34 and the ports 30,32 on either side thereof, the motor 50 can be started to provide a movement; e.g., rotational, reciprocal, etc. of the elongated member 52 as required to achieve the desired fluid flow through the lumen 42 past the blockage of the vessel 22 caused by the balloon 34 of the catheter 20. The movement of the elongated member 52 might be varied as required to create the desired fluid flow. Moreover, the fluid moving mechanism 54 on the end of the elongated member 52 might be replaceable to allow interchangeability of fluid moving mechanisms of varying configurations and sizes. Once treatment of the body vessel 22 is completed or the pump apparatus 26 is no longer required, the elongated member 52 and its associated fluid moving mechanism 54 can be removed from the lumen 42 of the catheter 20.

As previously mentioned, yet another advantage of the present invention is that the preferred embodiment can be used with a catheter whose perfusion lumen is open at the distal end 36 so as to allow insertion of a guide wire into the perfusion lumen. In those situations where a guide wire is already in place in the vessel but the catheter 20 is not present, the proximal end of the guide wire can be inserted into the lumen 42 at its distal end 36, and the catheter 20 then guided along the guide wire to the blockage location in the vessel. The guide wire can then be removed from the catheter, and the elongated member 52 with the fluid moving mechanism 54 inserted into the lumen 42 of the catheter 20 and guided to the location of the balloon 34.

Similarly, if there is no guide wire or catheter in the body vessel 22, a guide wire can be inserted by conventional techniques and the balloon catheter 20 guided along the guide wire to the desired location. The guide wire can then be removed and the elongated member 52 of the pump apparatus 26 inserted. If the initial guide wire is located in a different lumen then where the intracatheter pump apparatus elongated member 52 is located, it need not be necessarily removed.

The design of the intracatheter pump of the present invention is such that it can also function as a conventional guide wire, thereby doing away with the requirement for a separate guide wire. This would also simplify the process using the intracatheter pump of the present invention since the steps of removing the guide wire and inserting the elongated member 52 would be eliminated.

It is to be understood, that even though numerous characteristics and advantages of the invention have been set forth in the foregoing description, together with details of the structure and function of the invention, the disclosure is illustrative only, and changes may be made in detail, especially in matters of shape, size, and arrangement of the parts within the principles of the invention to the full extent indicated by the broad general meaning of the terms in which the appended claims are expressed.

What is claimed is:

1. An intracatheter perfusion pump apparatus for pumping fluids into and out of a lumen of a catheter, the pump apparatus being sized to fit within a coronary artery, comprising:
   an elongated member having a proximal end and a distal end and being positionable in the lumen of the catheter,
   a motor mechanically connectable to the proximal end of the elongated member for moving the elongated member, and
   a fluid moving mechanism attached to the elongated member proximate the distal end thereof, movement of the fluid moving mechanism causing longitudinal movement of fluids through the lumen.

2. An apparatus in accordance with claim 1, wherein the fluid moving mechanism has a helical configuration.

3. An apparatus in accordance with claim 1, wherein the fluid moving mechanism includes an elongated cylindrical member having a ridge about the circumference thereof arranged in a longitudinal helix whereby as the member is rotated the pump apparatus will pump fluids.

4. An apparatus in accordance with claim 1, wherein the fluid moving mechanism includes a substantially flat ribbon member twisted in a longitudinal helical pattern.

5. An apparatus in accordance with claim 1, wherein the elongated member is rotatable at different rates by the motor.

6. A pump apparatus in accordance with claim 1, wherein the fluid moving mechanism includes a rotor attached to the elongated member proximate the distal end.

7. An apparatus in accordance with claim 1, wherein the fluid moving mechanism includes an impeller which moves fluid in the direction of desired fluid flow as the elongated member is rotated.

8. An intracatheter perfusion pump in accordance with claim 1, providing a fluid flow of roughly five to sixteen cubic centimeters per minute.

9. An intracatheter perfusion pump in accordance with claim 1 wherein said fluid movement mechanism is rotatable in either direction to cause movement of fluids through the lumen in either direction.

10. A system for localized perfusion of fluids, comprising:
    a catheter having at least one lumen, the lumen having at least two longitudinally spaced-apart fluid communication ports;
    an elongated member having a proximal end and a distal end and being positionable in the lumen of the catheter;
    a motor mechanically connectable to the proximal end of the elongated member for moving the elongated member; and a fluid-moving mechanism attached to the elongated member proximate the distal end thereof, movement of the fluid-moving mechanism causing localized fluid flow within the lumen of the catheter between the spaced-apart fluid communication ports, the catheter, elongated member and motor sized to fit within the coronary artery.

11. A pump apparatus for pumping fluids into and out of a lumen of a catheter, comprising:
    an elongated member having a proximal end and a distal end positionable in the catheter,
    power means mechanically connectable to the proximal end of the elongated member for imparting longitudinal reciprocating motion, and
    a fluid moving mechanism positioned proximate the distal end of the elongated member for moving fluids upon longitudinal reciprocating movement thereof by the power means.

12. An apparatus in accordance with claim 11, wherein the fluid moving mechanism is a piston.

13. An apparatus in accordance with claim 11, wherein the fluid moving mechanism is flexible whereby the elongated member and the fluid moving mechanism can be used as a guide wire.

14. A method, of pumping fluids through a section of a catheter lumen disposed in a coronary artery, the lumen having at least two longitudinally spaced apart fluid communication ports, the method comprising the steps of:
    inserting an elongated member, having a fluid moving mechanism attached to a distal end thereof, into the lumen of the catheter in the coronary artery; and
    moving the elongated member such that the fluid moving mechanism moves fluid longitudinally of the lumen between the two longitudinally spaced apart ports within the coronary artery.

15. A system for localizing perfusion of fluids, comprising:
    a catheter having at least one lumen, the lumen having at least two longitudinally spaced-apart fluid communication ports;
    an elongated member having a proximal end and a distal end and being positionable in the lumen of the catheter;
    a motor mechanically connectable to the proximal end of the elongated member for moving the elongated member; and
    a fluid-moving mechanism attached to the elongated member proximate the distal end thereof, movement of the fluid-moving mechanism causing localized fluid flow within the lumen of the catheter between the spaced-apart fluid communication ports, the catheter, elongated member and motor sized to fit within the coronary artery.

* * * * *

UNITED STATES PATENT AND TRADEMARK OFFICE
CERTIFICATE OF CORRECTION

PATENT NO. : 5,092,844

DATED : March 3, 1992

INVENTOR(S) : Robert S. Schwartz et al.

It is certified that error appears in the above-identified patent and that said Letters Patent is hereby corrected as shown below:

On the cover page under the heading "FOREIGN PATENT DOCUMENTS", "France" should read as --European Patent Office--.

In the drawings, Sheet 2, Fig. 4, the reference numeral "70" should be applied to the impeller attached to the end of the elongated member 52 of the fluid moving mechanism 54''.

In the drawings, Sheet 2, Fig. 5A, blood flow directional arrows with the reference numeral "88" applied thereto should be indicated in the lumen 42 as similarly illustrated in Fig. 4.

In column 7, line 12, reference numeral "72" should read as --84,86--.

In column 7, line 48, "30" should read as --32--.

In column 7, lines 50 and 51, delete the phrase "also referred to as the at rest position,".

In column 10, lines 41 through 58, the wording of claim 15 which begins "A system for localizing perfusion of fluids..." and ends with "...sized to fit within the coronary artery." should read as --A method of perfusing fluids past a location within a coronary artery, the method comprising the steps of:
   inserting an elongated member having a fluid moving mechanism attached to a distal end thereof, into the coronary artery;

UNITED STATES PATENT AND TRADEMARK OFFICE
CERTIFICATE OF CORRECTION

PATENT NO. : 5,092,844

DATED : March 3, 1992

INVENTOR(S) : Robert S. Schwartz et al.

It is certified that error appears in the above-identified patent and that said Letters Patent is hereby corrected as shown below:

> threading a catheter along the elongated member to proximate the location of the coronary artery by insertion of the proximal end of the elongated member into a perfusion lumen of the catheter; and moving the elongated member by a power source such that the fluid moving mechanism moves fluid longitudinally of the perfusion lumen.--

Signed and Sealed this

Seventeenth Day of August, 1993

*Attest:*

BRUCE LEHMAN

*Attesting Officer*     *Commissioner of Patents and Trademarks*